US011446342B2

(12) United States Patent
Ma et al.

(10) Patent No.: US 11,446,342 B2
(45) Date of Patent: *Sep. 20, 2022

(54) COMPOSITE PROBIOTICS AND USE THEREOF

(71) Applicant: INFINITUS (CHINA) COMPANY LTD., Guangdong (CN)

(72) Inventors: Fangli Ma, Guangdong (CN); Wei Chen, Guangdong (CN); Gang Wang, Guangdong (CN); Xiaofeng Zhu, Guangdong (CN); Yuanyuan Wang, Guangdong (CN); Junyong Xiao, Guangdong (CN); Hao Zhang, Guangdong (CN); Jianxin Zhao, Guangdong (CN)

(73) Assignee: INFINITUS (CHINA) COMPANY LTD., Guangdong (CN)

( * ) Notice: Subject to any disclaimer, the term of this patent is extended or adjusted under 35 U.S.C. 154(b) by 216 days.

This patent is subject to a terminal disclaimer.

(21) Appl. No.: 16/520,366

(22) Filed: Jul. 24, 2019

(65) Prior Publication Data
US 2020/0261519 A1 Aug. 20, 2020

(30) Foreign Application Priority Data
Feb. 20, 2019 (CN) .......................... 201910127922.1

(51) Int. Cl.
*A61K 9/19* (2006.01)
*A61K 35/747* (2015.01)
*A61K 35/745* (2015.01)

(52) U.S. Cl.
CPC .............. *A61K 35/747* (2013.01); *A61K 9/19* (2013.01); *A61K 35/745* (2013.01)

(58) Field of Classification Search
CPC .... A61K 35/74; A61K 35/745; A61K 35/747; A61K 35/741; A61K 2035/115; A61K 35/742; A61K 35/744; A61K 9/0053; A61K 9/19; A61K 31/7004; A61K 31/7016; A61K 31/715; A61K 35/39; A61K 38/46; A61K 9/0031; A61K 2300/00; A61K 38/00; A61K 38/10; A61K 31/575; A61K 2035/11; A61K 2039/5158; A61K 2039/55505; A61K 2039/55566; A61K 2039/6006; A61K 35/37; A61K 39/0011; A61K 39/0225; A61K 31/56; A61K 38/164; A61K 47/26; A61K 9/0095; A61K 9/10; A61K 9/1605; A61K 9/2004; A61K 9/4841; A61P 1/00; A61P 29/00; A61P 37/00; A61P 43/00; A61P 1/04; A61P 35/00; A61P 1/08; A61P 1/12; A61P 1/16; A61P 3/04; A61P 9/00; A61P 9/04; A61P 9/12; A61P 31/04; A61P 31/06; A61P 31/00; A61P 3/00; Y02A 50/30; A23V 2002/00; A23V 2200/332; A23V 2200/30; A23V 2200/3262; C07K 7/08; C07K 14/4705; C12N 2710/16122; C12N 2710/16222; C12N 1/20; C12Q 1/6883; C12Q 1/689; C12Q 2600/158; G01N 33/56911; A23L 33/135; A23L 33/00; A61B 17/00491; A61B 17/0057; A61B 17/12118; A61B 17/12181; A61B 17/3468; A61B 18/18; A61B 2017/00411; A61B 2017/0065; A61B 2017/00876; A61B 2017/1205; A61F 2/82;

(Continued)

(56) References Cited

U.S. PATENT DOCUMENTS

| | | | |
|---|---|---|---|
| 10,022,408 B2 * | 7/2018 | Leser | ...................... A61P 25/22 |
| 10,968,495 B2 * | 4/2021 | Ma | ......................... A23L 33/135 |
| 2015/0051204 A1 | 2/2015 | Agreda Navajas et al. | |

(Continued)

FOREIGN PATENT DOCUMENTS

| | | | |
|---|---|---|---|
| CN | 103446139 A | 12/2013 | |
| CN | 103596949 A | 2/2014 | |

(Continued)

OTHER PUBLICATIONS

The 1st Office Action dated May 19, 2020 for the Chinese Application No. 201910 127 922.1.

(Continued)

Primary Examiner — Taeyoon Kim
Assistant Examiner — Tiffany M Gough
(74) Attorney, Agent, or Firm — Yue (Robert) Xu; Apex Attorneys at Law, LLP

(57) ABSTRACT

The present disclosure relates to the field of microbial technology, and discloses a composite probiotics and the use thereof. The composite probiotics in the present disclosure is consisted of *Bifidobacterium adolescentis* CCFM8630, *Lactobacillus reuteri* CCFM8631, *Lactobacillus rhamnosus* CCFM1044 and *Lactobacillus casei* CCFM711, whose effect of alleviating metabolic syndrome is significantly better than that of CCFM8630 or CCFM8631 alone or combination of the two, especially in aspects of lowering contents of serum low density lipoprotein, total cholesterol, and liver triglyceride and contents of serum alanine aminotransferase, aspartate aminotransferase, alkaline phosphatase and IFN-γ, and increasing contents of liver glutathione and superoxide dismutase, etc. The extent of decrease or increase is increased by 7.91% to 837.31% compared with the formulations of CCFM8630 or CCFM8631 alone or combination of the two probiotics. The combination of the four probiotics can achieve a significant synergistic effect.

3 Claims, 5 Drawing Sheets

(58) Field of Classification Search
CPC ............ A23Y 2220/17; A23Y 2220/71; A23Y 2220/73; A23Y 2300/19; C12R 1/00
See application file for complete search history.

(56) References Cited

U.S. PATENT DOCUMENTS

| | | |
|---|---|---|
| 2018/0360092 A1 | 12/2018 | Kiely |
| 2019/0046545 A1 | 2/2019 | Binia |
| 2019/0112674 A1 | 4/2019 | Wang et al. |
| 2019/0112675 A1 | 4/2019 | Ma et al. |
| 2020/0121738 A1 | 4/2020 | Cutcliffe |

FOREIGN PATENT DOCUMENTS

| | | | |
|---|---|---|---|
| CN | 103656076 A | 3/2014 | |
| CN | 103977014 A | 8/2014 | |
| CN | 105995972 | * 12/2016 | ............... A23L 2/38 |
| CN | 107523526 A | 12/2017 | |
| CN | 107699517 A | 2/2018 | |
| CN | 108295098 A | 7/2018 | |
| CN | 108495637 A | 9/2018 | |
| CN | 109312297 A | 2/2019 | |
| KR | 20180105622 A | 9/2018 | |
| WO | 2015172191 A1 | 11/2015 | |
| WO | 2018106844 A1 | 6/2018 | |

OTHER PUBLICATIONS

Soyoung Park et al. Cholesterol-lowering effect of Lactobacillus rhamnosus BFE5264 and its influence on the gut microbiome and propionate level in a murine model, PLoS One, vol. 13, No. 8, Aug. 28, 2018, pp. 1-15.

* cited by examiner

COMPOSITE PROBIOTICS AND USE THEREOF

CROSS REFERENCE TO RELATED APPLICATIONS

This application claims the priority of Chinese Patent Application No. 201910127922.1, filed on Feb. 20, 2019, and titled with "COMPOSITE PROBIOTICS AND USE THEREOF", and the disclosures of which are hereby incorporated by reference.

FIELD

The present disclosure relates to the field of microbial technology, specifically to composite probiotics and uses thereof, especially to composite probiotics for alleviating metabolic syndrome and uses thereof.

BACKGROUND

Metabolic syndrome is a group of diseases closely related to obesity, diabetes, hypertension and cardiovascular diseases. The clinical manifestations are abnormal glucose tolerance, overweight or obesity, dyslipidemia, and hypertension, etc. Numerous studies have shown that metabolic syndrome is a major cause of cardiovascular disease. People with metabolic syndrome are also more likely to develop an inflammation, and are also susceptible to other diseases, such as polycystic ovarian syndrome, fatty liver, cholesterol gallstone, asthma, abnormal sleep and certain cancers. In addition, metabolic syndrome has a significant relationship with the prevalence rate and mortality of coronary atherosclerotic heart disease and type 2 diabetes. Currently, the prevalence rate of metabolic syndrome worldwide is rapidly increasing, including in developing countries. A population survey conducted in China found that the prevalence rate of metabolic syndrome in population of mainland China in 2016 was 24.5%. Another study showed that the prevalence rate of metabolic syndrome increased from 13.6% in 1993-1996 to 25.5% in 2005-2008.

The treatment of metabolic syndrome is mainly to control and improve the risk factors. The traditional treatment method is drug therapy. For example, CN103977014A discloses a drug for treating metabolic syndrome, including Akebia saponin and curcumin, which can prevent and treat metabolic syndrome by regulating the metabolic processes of proteins, lipids and carbohydrates of patients. CN103596949A discloses a novel compound molecular structure which has a therapeutic effect on diabetes and metabolic syndrome. CN103446139A discloses a pharmaceutical combination for treating metabolic syndrome, including puerarin, cinnamic acid and berberine hydrochloride, and the combination has effects of improving insulin resistance and at the same time lowering blood glucose, lowering blood pressure, lowering blood lipid and improving abdominal obesity. Although drug treatment is effective, it is accompanied by a certain degree of side effects, and it requires a long-term medication, and the body is prone to drug dependence.

A large number of studies have reported that the intestinal flora plays an extremely important role in the physiological metabolism of human body. The structural imbalance of intestinal flora is associated with a variety of diseases, including gastrointestinal diseases (irritable bowel syndrome and inflammatory bowel disease, etc.), metabolic diseases (obesity, hyperlipidemia, diabetes, etc.). The occurrence of metabolic syndrome is also closely related to the imbalance of intestinal flora. The commonly used intestinal flora regulating preparations include probiotics and prebiotics, etc. For example, CN107699517A discloses a *Bifidobacterium adolescentis* and uses thereof, which significantly improves the pathological damage of liver and duodenum, the increase of contents of triglyceride and total cholesterol in serum and oral glucose tolerance of rats with metabolic syndrome caused by high-sugar and high-fat diet. CN107523526A discloses a *Lactobacillus reuteri* and uses thereof, which can reduce serum blood lipid level and blood glucose level in serum of rats with metabolic syndrome. CN108295098A discloses a synbiotic composition for assisting to lower blood glucose, which comprises prebiotics and probiotics, and stimulates the immune function of intestinal tract to restore the intestinal function to normal, maintain the micro-ecological balance of human body, and achieve the effect of lowering blood glucose. CN103656076A discloses a probiotic-Chinese herbal medicine compound preparation having a function of lowering blood glucose. However, all the above patents use a single probiotic or a combination of probiotics and prebiotics or Chinese herbal medicines to alleviate the metabolic syndrome. At present, there are few studies on probiotics compounding formulations of mutiple strains that can synergistically improve metabolic syndrome.

SUMMARY

In view of this, an object of the present disclosure is to provide composite probiotics, which can be used for alleviating metabolic syndrome.

In order to achieve the object of the present disclosure, the following technical solutions are used in the present disclosure.

Composite probiotics, consisting of *Bifidobacterium adolescentis* CCFM8630, *Lactobacillus reuteri* CCFM8631, *Lactobacillus rhamnosus* CCFM1044 and *Lactobacillus casei* CCFM711.

Preferably, ratio of viable count of *Bifidobacterium adolescentis* CCFM8630, *Lactobacillus reuteri* CCFM8631, *Lactobacillus rhamnosus* CCFM1044 and *Lactobacillus casei* CCFM711 is 1:(1-10):(1-10):(1-10).

In the present disclosure, a method for preparing the composite probiotics is also provided, comprising, respectively inoculating bacteria solutions of *Bifidobacterium adolescentis* CCFM8630, *Lactobacillus reuteri* CCFM8631, *Lactobacillus rhamnosus* CCFM1044 and *Lactobacillus casei* CCFM711 to modified MRS culture mediums, culturing at 34-39° C. under anaerobic conditions for 18-24 h, and collecting thalli; respectively resuspending the thalli with a freeze-drying protective agent so that the content of each thallus is above $10^{10}$ CFU/mL, then culturing the suspension at 37° C. under anaerobic conditions for 40-60 min, drying to obtain freeze-dried bacterial powder of each thallus, resuspending and diluting, and spreading on a plate to determine the viable count in the bacterial powder; and compounding and mixing the freeze-dried bacterial powders of *Bifidobacterium adolescentis* CCFM8630, the freeze-dried bacterial powder of *Lactobacillus reuteri* CCFM8631, the freeze-dried bacterial powder of *Lactobacillus rhamnosus* CCFM1044 and the freeze-dried bacterial powder of *Lactobacillus casei* CCFM711 in a certain proportion to achieve a desired ratio of viable count.

Preferably, the modified MRS (mMRS) culture medium is an MRS culture medium that contains 0.05% of L-cysteine hydrochloride; the freeze-drying protective agent is an aqueous solution that contains 100 g/L-150 g/L skimmed milk powder, 30 g/L-100 g/L sucrose and 30 g/L-100 g/L trehalose; and the drying is a vacuum freeze drying that is carried out after pre-freezing at −15 to 20° C. for 8 to 14 h.

In the present disclosure, use of the composite probiotics in the preparation of products for alleviating metabolic syndrome is also provided.

Preferably, the product is a health care food or a medicine.

Preferably, the health care food is a microbial agent or a fermented food.

In the present disclosure, a microbial agent containing the composite probiotics is also provided.

Preferably, the viable count of the composite probiotics is more than $1 \times 10^{11}$ CFU/g.

The present disclosure has the following beneficial technical effects:

the composite probiotics consisting of *Bifidobacterium adolescentis* CCFM8630, *Lactobacillus reuteri* CCFM8631, *Lactobacillus rhamnosus* CCFM1044 and *Lactobacillus casei* CCFM711 in the present disclosure is a natural, safe micro-ecological preparation that can effectively alleviate metabolic syndrome, whose effect of alleviating metabolic syndrome is significantly better than that of CCFM8630 or CCFM8631 alone or combination of CCFM8630 and CCFM8631, especially in aspects of lowering contents of serum low density lipoprotein (LDL-C), total cholesterol (TC), and liver triglyceride (TG) and contents of serum alanine aminotransferase (ALT), aspartate aminotransferase (AST), alkaline phosphatase (ALP) and IFN-γ, and increasing contents of liver glutathione and superoxide dismutase, etc. The extent of decrease or increase is increased by 7.91%-837.31% compared with the formulations of CCFM8630 or CCFM8631 alone or combination of the two probiotics. The combination of four probiotics *Bifidobacterium adolescentis* CCFM8630, *Lactobacillus reuteri* CCFM8631, *Lactobacillus rhamnosus* CCFM1044 and *Lactobacillus casei* CCFM711 together can achieve a significant synergistic effect. The composite probiotics in the present disclosure may be used in the preparation of a health care food or a medicine for alleviating metabolic syndrome, which has a very broad application prospect.

DESCRIPTION OF MICROBIOLOGICAL PRESERVATION

CCFM8630, classified nomenclature: *Bifidobacterium adolescentis*, is preserved at the General Microbiology Center of the China Microbial Culture Preservation Committee on Jul. 7, 2017; the preservation address is Institute of Microbiology, Chinese Academy of Sciences, No. 3 in No. 1 Yard, Beichen West Road, Chaoyang District, Beijing, China; the preservation number is CGMCC 14395.

CCFM8631, classified nomenclature: *Lactobacillus reuteri*, is preserved at the General Microbiology Center of the China Microbial Culture Preservation Committee on Jul. 7, 2017; the preservation address is Institute of Microbiology, Chinese Academy of Sciences, No. 3 in No. 1 Yard, Beichen West Road, Chaoyang District, Beijing, China; the preservation number is CGMCC 14394.

CCFM1044, classified nomenclature: *Lactobacillus rhamnosus*, is preserved at Guangdong Provincial Microbial Culture Collection on Jan. 21, 2019; the preservation address is Guangdong Institute of Microbiology, 5th Floor, Building 59, No. 100 Yard, Xianlie Middle Road, Guangzhou; the preservation number is GDMCC No: 60540.

CCFM711, classified nomenclature: *Lactobacillus casei*, is preserved at Guangdong Provincial Microbial Culture Collection on Jan. 21, 2019; the preservation address is Guangdong Institute of Microbiology, 5th Floor, Building 59, No. 100 Yard, Xianlie Middle Road, Guangzhou; the preservation number is GDMCC No: 60539.

BRIEF DESCRIPTION OF DRAWINGS

In order to more clearly illustrate the embodiments of the present invention or the technical solutions in the prior art, the figures to be used in the embodiments or the prior art will be briefly described below.

Figure 1:
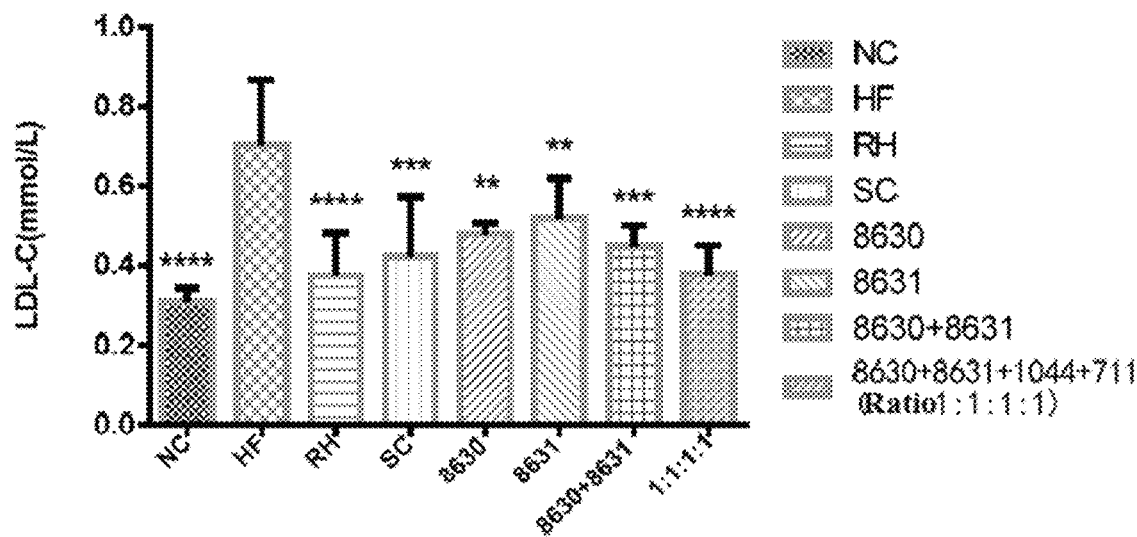
FIG. 1 is a graph showing the effects of different probiotic compounding intervention groups in Example 3 of the present disclosure on alleviating serum LDL-C content increasing in mice having high-fat diet induced metabolic syndrome.

The above figures were plotted with Graphpad Prism5, and comparison among each experimental group was done using LSD test mean comparison. Compared with the model group, if P<0.05, it is marked with *. If P<0.01, it is marked with . If P<0.001, it is marked with *. If P<0.0001, it is marked with ****.

DETAILED DESCRIPTION

In the present disclosure, composite probiotics and uses thereof are disclosed. One of ordinary skill in the art can learn from the contents of this document and appropriately improve the process parameters. It should be specially indicated that all such alternatives and modifications are obvious to one of ordinary skill in the art and are considered to be included in the present disclosure. The methods and products of the present disclosure have been described in preferred embodiments. It will be apparent that one of ordinary skill in the art can change or appropriately modify and combine the methods described herein to implement and apply the present invention without departing from the content, spirit and scope of the disclosure.

In order to achieve the objects of the present disclosure, the following technical solutions are used in the present disclosure.

Composite probiotics consisting of *Bifidobacterium adolescentis* CCFM8630, *Lactobacillus reuteri* CCFM8631, *Lactobacillus rhamnosus* CCFM1044 and *Lactobacillus casei* CCFM711 are provided.

The *Bifidobacterium adolescentis* CCFM8630 in the present disclosure is preserved at the General Microbiology Center of the China Microbial Culture Preservation Committee on Jul. 7, 2017; the preservation address is Institute of Microbiology, Chinese Academy of Sciences, No. 3 in No. 1 Yard, Beichen West Road, Chaoyang District, Beijing, China; the preservation number is CGMCC 14395.

The *Lactobacillus reuteri* CCFM8631 in the present disclosure is preserved at the General Microbiology Center of the China Microbial Culture Preservation Committee on Jul. 7, 2017; the preservation address is Institute of Microbiology, Chinese Academy of Sciences, No. 3 in No. 1 Yard, Beichen West Road, Chaoyang District, Beijing, China; the preservation number is CGMCC 14394.

The *Lactobacillus rhamnosus* CCFM1044 in the present disclosure is preserved at Guangdong Provincial Microbial Culture Collection on Jan. 21, 2019; the preservation address is Guangdong Institute of Microbiology, 5th Floor, Building 59, No. 100 Yard, Xianlie Middle Road, Guangzhou; the preservation number is GDMCC No: 60540.

The *Lactobacillus casei* CCFM711 in the present disclosure is preserved at Guangdong Provincial Microbial Culture Collection on Jan. 21, 2019; the preservation address is Guangdong Institute of Microbiology, 5th Floor, Building 59, No. 100 Yard, Xianlie Middle Road, Guangzhou; the preservation number is GDMCC No: 60539.

Wherein, preferably, the ratio of viable count of *Bifidobacterium adolescentis* CCFM8630, *Lactobacillus reuteri* CCFM8631, *Lactobacillus rhamnosus* CCFM1044 and *Lactobacillus casei* CCFM711 in the composite probiotics is 1:(1-10):(1-10):(1-10).

In some embodiments, the ratio of viable count of *Bifidobacterium adolescentis* CCFM8630, *Lactobacillus reuteri* CCFM8631, *Lactobacillus rhamnosus* CCFM1044 and *Lactobacillus casei* CCFM711 in the composite probiotics is 1:1:1:1, 1:1:5:5, 1:5:10:2 or 1:10:2:10.

In the present disclosure, a method for preparing the composite probiotics is also provided, comprising, respectively inoculating bacteria solutions of *Bifidobacterium adolescentis* CCFM8630, *Lactobacillus reuteri* CCFM8631, *Lactobacillus rhamnosus* CCFM1044 and *Lactobacillus casei* CCFM711 to modified MRS culture mediums, culturing at 34-39° C. under anaerobic conditions for 18-24h, and collecting thalli; respectively resuspending the thalli with a freeze-drying protective agent so that the content of each thallus is above $10^{10}$ CFU/mL, then culturing the suspension at 37° C. under anaerobic conditions for 40-60 min, drying to obtain freeze-dried bacterial powder of each thallus, resuspending and diluting, and spreading on a plate to determine the viable count in the bacterial powder; and compounding and mixing the freeze-dried bacterial powders of *Bifidobacterium adolescentis* CCFM8630, the freeze-dried bacterial powder of *Lactobacillus reuteri* CCFM8631, the freeze-dried bacterial powder of *Lactobacillus rhamnosus* CCFM1044 and the freeze-dried bacterial powder of *Lactobacillus casei* CCFM711 in a certain proportion to achieve a desired ratio of viable count.

In the method for preparing the composite probiotics of the present disclosure, the modified MRS (mMRS) culture medium is an MRS culture medium that contains 0.05% of L-cysteine hydrochloride. The specific preparation method is mixing tryptone 10 g, beef extract 10 g, yeast powder 5 g, glucose 20 g, sodium acetate 5 g, diammonium hydrogen citrate 2 g, dipotassium hydrogen phosphate 2 g, magnesium sulfate heptahydrate 0.5 g, Tween 80 1 mL, manganese sulfate monohydrate 0.25 g and cysteine hydrochloride 0.5 g, and adjusting the volume to 1000 mL with water, adjusting the pH to 6.8, and sterilizing at 119-123° C. for 15-25 min.

In the method of the present disclosure, the freeze-drying protective agent is an aqueous solution that contains 100 g/L-150 g/L skimmed milk powder, 30 g/L-100 g/L sucrose and 30 g/L-100 g/L trehalose. That is, the freeze-drying protective agent is consisted of skimmed milk powder, glucose, trehalose and water, wherein the concentration of skimmed milk powder is 100 g/L-150 g/L, the concentration of glucose is 30 g/L-100 g/L, and the concentration of trehalose is 30 g/L-100 g/L.

Preferably, in the method of the present disclosure, after culturing in the modified MRS culture medium, the collected thalli are washed with phosphate buffer solution for 2 to 4 times, and the phosphate buffer has a pH of 6.8 to 7.2.

In the method of the present disclosure, the drying may be carried out by any bacteria solution drying process, for example vacuum freeze drying. In some embodiments, the drying in the method of the present disclosure is vacuum freeze drying that is carried out after pre-freezing at −15 to 20° C. for 8 to 14 h.

In some embodiments, the method for preparing the composite probiotics in the present disclosure comprises the following steps.

(1) Preparing a Modified MRS Culture Medium (mMRS)

Tryptone 10 g, beef extract 10 g, yeast powder 5 g, glucose 20 g, sodium acetate 5 g, diammonium hydrogen citrate 2 g, dipotassium hydrogen phosphate 2 g, magnesium sulfate heptahydrate 0.5 g, Tween 80 1 mL, manganese sulfate monohydrate 0.25 g and cysteine hydrochloride 0.5 g are added into 1 L water, and adjusting the pH of the culture medium to 6.8 to 7.0.

(2) Preparing a Freeze-Drying Probiotic Protective Agent.

100 g-150 g skimmed milk powder, 30 g-100 g sucrose and 30 g-100 g trehalose are added into 1 L water.

(3) Preparing Freeze-Dried Bacterial Powders.

*Bifidobacterium adolescentis* CCFM8630, *Lactobacillus reuteri* CCFM8631, *Lactobacillus rhamnosus* CCFM1044 and *Lactobacillus casei* CCFM711 are respectively taken from a condition at −80° C., streaked on a solid culture medium plate to obtain a single colony, and cultured in an anaerobic workstation at 34-39° C. for 36 h-48 h. Single colonies are respectively picked and inoculated into modified MRS liquid culture medium, cultured in the anaerobic workstation at 34-39° C. for 18 h-24 h, and then respectively inoculated in larger volume of liquid culture medium in an inoculum size of 2% to 4% (v/v). After culturing in an anaerobic workstation at 34-39° C. for 18 h-24 h, the resultants are centrifuged at 5000 rpm for 15 min to obtain a bacterial sludge. The bacterial sludge is washed with phosphate buffer (pH 6.8 to 7.2) for 2 to 3 times, and resuspended with freeze-drying protective agent having a mass equal to the bacterial sludge, so that the content of the thalli reaches 1010 CFU/mL or more. Thereafter, the suspension is pre-incubated under anaerobic conditions at 37° C. for 40 to 60 min, and then pre-freezed at −15 to −20° C. for 8 to 14 h, and finally vacuum freeze-drying is carried out to respectively obtain the freeze dried bacterial powders of *Bifidobacterium adolescentis* CCFM8630, *Lactobacillus reuteri* CCFM8631, *Lactobacillus rhamnosus* CCFM1044 and *Lactobacillus casei* CCFM711.

(4) Preparing the Composite Probiotics.

The *Bifidobacterium adolescentis* CCFM8630, *Lactobacillus reuteri* CCFM8631, *Lactobacillus rhamnosus* CCFM1044 and *Lactobacillus casei* CCFM711 are compounded and mixed in a certain proportion to achieve a desired ratio of viable count.

In some embodiments, the present invention studies the effect of composite probiotics consisting of *Bifidobacterium adolescentis* CCFM8630, *Lactobacillus reuteri* CCFM8631, *Lactobacillus rhamnosus* CCFM1044 and *Lactobacillus casei* CCFM711 on metabolic syndrome. The results show that the composite probiotics have an effect on alleviating liver injury of rat having high-fat diet induced metabolic syndrome, obviously lowering contents of liver triglyceride, serum alanine aminotransferase (ALT), aspartate aminotransferase (AST), alkaline phosphatase (ALP), IFN-γ and increasing liver antioxidant capacity, etc. The extent of decrease or increase is increased by 7.91%-837.31% compared with formulations of CCFM8630 or CCFM8631 alone or a combination of the two probiotics. The combination of four probiotics *Bifidobacterium adolescentis* CCFM8630, *Lactobacillus reuteri* CCFM8631, *Lactobacillus rhamnosus* CCFM1044 and *Lactobacillus casei* CCFM711 together can achieve a significant synergistic effect.

Thus, the present disclosure provides use of the composite probiotics in the preparation of products for alleviating metabolic composition.

Therein, the metabolic syndrome is abnormal blood lipid, liver injury, inflammation and oxidative stress, etc.

In the present disclosure, the product includes but is not limited to a health care food or a medicine.

In the product of the present disclosure, daily total intake viable count of the four bacteria is not less than $2\times10^8$ CFU.

Therein, the health care food includes but is not limited to a microbial agent or a fermented food.

Further, the present disclosure provides a microbial agent containing the composite probiotics.

Preferably, viable count of the composite probiotics in the microbial agent is not less than $1\times10^{11}$ CFU/g.

In the present disclosure, the microbial agent may be prepared by a conventional method.

The present disclosure also provides a fermented food, which is produced by fermenting using the above composite probiotics as a fermenting agent.

The fermented food is fermented dairy products, fermented bean products, or fermented fruit and vegetable products.

The fermented dairy products include but are not limited to yogurt, sour cream and cheese. The fermented bean products include but are not limited to soymilk, fermented soya beans, and soybean paste. The fruit and vegetables in the fermented fruit and vegetable products include but are not limited to cucumber, carrot, beet, celery and cabbage.

The present disclosure also provides a pharmaceutical formulation, comprising an effective amount of the composite probiotics and a pharmaceutically acceptable adjuvant.

The pharmaceutically acceptable adjuvant includes one or more of filler, binder, wetting agent, disintegrant, lubricant, and flavoring agent.

In some embodiments of the present disclosure, the pharmaceutical formulation is in the form of granule, capsule, tablet, pill or oral solution.

The present disclosure has the following beneficial technical effects:

the composite probiotics consisting of *Bifidobacterium adolescentis* CCFM8630, *Lactobacillus reuteri* CCFM8631, *Lactobacillus rhamnosus* CCFM1044 and *Lactobacillus casei* CCFM711 in the present disclosure is a natural, safe micro-ecological preparation that can effectively alleviate metabolic syndrome, whose effect of alleviating metabolic syndrome is significantly better than that of CCFM8630 or CCFM8631 alone or combination of CCFM8630 and CCFM8631, especially in aspects of lowering contents of serum low density lipoprotein (LDL-C), total cholesterol (TC), and liver triglyceride (TG) and contents of serum alanine aminotransferase (ALT), aspartate aminotransferase (AST), alkaline phosphatase (ALP) and IFN-γ, and increasing liver antioxidant capacity, etc. The extent of decrease or increase is increased by 7.91%-837.31% compared with the formulations of CCFM8630 or CCFM8631 alone or combination of the two probiotics. The combination of four probiotics *Bifidobacterium adolescentis* CCFM8630, *Lactobacillus reuteri* CCFM8631, *Lactobacillus rhamnosus* CCFM1044 and *Lactobacillus casei* CCFM711 together can achieve a significant synergistic effect. The composite probiotics in the present disclosure may be used in the preparation of a health care food or a medicine for alleviating metabolic syndrome, which has a very broad application prospect.

In order to further understand the present disclosure, the technical solutions in the embodiments of the present disclosure will be clearly and completely described hereinafter in conjunction with the embodiments of the present disclosure. It is apparent that the described embodiments are only a part of the embodiments of the present disclosure, and not all of the embodiments. All other embodiments obtained by one of ordinary skill in the art based on the embodiments of the present disclosure without creative efforts are within the scope of protection of the present disclosure.

Unless otherwise stated, the reagents involved in the embodiments of the present invention are all commercially available products, which are all 1 commercially available.

Example 1

Composite Probiotics Have Good Tolerance to Simulated Gastric and Intestinal Fluid The *Bifidobacterium adolescentis* CCFM8630, *Lactobacillus reuteri* CCFM8631, *Lactobacillus rhamnosus* CCFM1044 and *Lactobacillus casei* CCFM711 preserved under a condition of −80° C. were respectively inoculated to modified MRS (mMRS) culture mediums, cultured in an anaerobic workstation at 37° C. for 36 h, and subcultured twice in an inoculum size of 2%-4% (v/v). The concentrations of viable bacterium of the *Bifidobacterium adolescentis* CCFM8630, *Lactobacillus reuteri* CCFM8631, *Lactobacillus rhamnosus* CCFM1044 and *Lactobacillus casei* CCFM711 culture solutions were adjusted to $5\times10^8$ CFU/ mL. 1 mL of the *Bifidobacterium adolescentis* CCFM8630, the *Lactobacillus reuteri* CCFM8631, the *Lactobacillus rhamnosus* CCFM1044 and the *Lactobacillus casei* CCFM711 culture solutions in a concentration of $5 \times 10^8$ CFU/mL were taken and mixed evenly. 1 mL of the mixed culture solution was taken and mixed with 9.0 mL simulated gastric fluid (mMRS culture medium containing 1% pepsin, having a pH of 2.5), and cultured under anaerobic conditions at 37° C. Samples were taken at $0^{th}$ h, $0.5^{th}$ h, $1^{st}$ h and $2^{nd}$ h, and spread and cultured on an mMRS solid culture medium, and plate colony counting was carried out, viable count was determined, and survival rate was calculated. The survival rate was a ratio of the logarithm of the viable count at the time of sampling in the culture solution to the logarithm of the viable count at the $0^{th}$ hour, expressed in %. The experimental results were shown in Table 1.

1 mL mixed culture solution was taken and added into 9 mL simulated intestinal fluid (containing 0.3% cholate, 1% trypsin, and mMRS culture medium having a pH of 8), and cultured under anaerobic conditions at 37° C. Samples were taken at $0^{th}$ h, $0.5^{th}$ h, $1^{st}$ h, $2^{nd}$ h, $3^{rd}$ h and $4^{th}$ h, and spread and cultured on an mMRS solid culture medium, and plate colony counting was carried out, viable count was determined, and survival rate was calculated. The survival rate was a ratio of the logarithm of the viable count at the time of sampling in the culture solution to the logarithm of the viable count at the $0^{th}$ hour, expressed in %. The experimental results were shown in Table 2.

TABLE 1

Tolerance of composite probiotics in simulated gastric fluid

| | Simulated gastric fluid | | |
|---|---|---|---|
| Treatment time (h) | 0.5 | 1 | 2 |
| Survival rate (%) | 83.1 | 78.9 | 73.0 |

TABLE 2

Tolerance of composite probiotics in simulated intestinal fluid

| | Simulated intestinal fluid | | | |
|---|---|---|---|---|
| Treatment time (h) | 0.5 | 1 | 2 | 3 | 4 |
| Survival rate (%) | 100 | 100 | 73.1 | 70.6 | 53.7 |

The results showed that the composite probiotics had relatively good tolerance to the simulated gastric fluid and simulated intestinal fluid.

Example 2

Composite Probiotics Have no Toxic and Side Effects on C57BL/6 J Mouse

The composite probiotics of *Bifidobacterium adolescentis* CCFM8630, *Lactobacillus reuteri* CCFM8631, *Lactobacillus rhamnosus* CCFM1044 and *Lactobacillus casei* CCFM711 in a ratio of viable count of 1:1:1:1 were resuspended in a 3% sucrose solution to prepare a bacterial suspension with a concentration of $1.0 \times 10^9$ CFU/mL. 8 heathy male C57BL/6 J mice with weights of 20 g-22 g were chosen. After one week of adaptive feeding, the mice were administered intragastrically with bacterial suspension with the above concentration once a day for one week, and the death and body weights were recorded. The experimental results were shown in Table 3.

TABLE 3

Body weight changes and mortality of the mice

| | Time (day) | | | | | | |
|---|---|---|---|---|---|---|---|
| | 1 | 2 | 3 | 4 | 5 | 6 | 7 |
| Weight (g) | 21.1 ± 0.9 | 21.3 ± 1.1 | 21.5 ± 1.3 | 21.6 ± 1.2 | 21.9 ± 0.8 | 22.2 ± 0.8 | 22.5 ± 0.9 |
| mortality | — | — | — | — | — | — | — |

Note:
—: no mouse died.

The results showed that administration of composite probiotics intragastrically with a concentration of $1.0 \times 10^9$ CFU/mL did not have significant effect on mice: the body weight gain did not change significantly, and no mouse died. The mice were normal in activity and had no obvious pathological appearance.

Example 3

Influence of Composite Probiotic on Serum LDL-C Level of Mouse Having High-Fat Diet-Induced Metabolic Syndrome The experimental animals were 48 5-week old SPF grade C57BL/6 male mice, which were purchased from Shanghai Slack Laboratory Animal Center. The high-fat feed was purchased from Nantong Trophic Animal Feed High-tech Co., Ltd. The model group was fed with TP23300 high-fat feed, and the normal control group was fed with TP23302 control feed. After the mice were adaptively feed for 7 days, the experiment started. The animals were given free access to food and water, the temperature was 22±2° C., the humidity was 55±5%, and the illumination was alternately 12 h bright and dark.

The experimental animals were randomly divided into 8 groups, comprising a blank control group (NC), a high-fat model control group (HF), a rosiglitazone control group (RH), a simvastatin control group (SC), a *Bifidobacterium adolescentis* CCFM8630 intervention group (8630), a *Lactobacillus reuteri* intervention group (8631), a *Bifidobacterium adolescentis* CCFM8630 and *Lactobacillus reuteri* CCFM8631 compounding group (8630+8631), a *Bifidobacterium adolescentis* CCFM8630, *Lactobacillus reuteri* CCFM8631, *Lactobacillus rhamnosus* CCFM1044 and *Lactobacillus casei* CCFM711 compounding group (8630+ 8631+1044+711). Each group contains 6 mice. The feeding environmental temperature was 20-26° C., the humidity was 40%-70% and the padding was replaced twice a week. In the *Bifidobacterium adolescentis* CCFM8630, *Lactobacillus reuteri* CCFM8631, *Lactobacillus rhamnosus* CCFM1044 and *Lactobacillus casei* CCFM711 compounding group, the ratio of viable count of *Bifidobacterium adolescentis* CCFM8630, *Lactobacillus reuteri* CCFM8631, *Lactobacillus rhamnosus* CCFM1044 and *Lactobacillus casei* CCFM711 was 1:1:1:1. Each mouse was administered intragastrically each day with probiotics with a concentration of $1.0 \times 10^9$ CFU/mL, which was resuspended in 3% sucrose solution, and the volume by intragastric administration was 0.2 mL, i.e., the total amount of probiotics administered intragastrically to each mouse was $2 \times 10^8$ CFU each day. The experimental groupings and treatment methods were shown in Table 4.

TABLE 4

Grouping of experimental animals

| Group | Number of mouse/ group | Treatment time | Feed | Treatment |
| --- | --- | --- | --- | --- |
| NC | 6 | 20 weeks | Control feed | Administering intragastrically with 0.2 mL 3% sucrose solution each day |
| HF | 6 | 20 weeks | High-fat feed | Administering intragastrically with 0.2 mL 3% sucrose solution each day |
| RH | 6 | 20 weeks | High-fat feed | Administering intragastrically with 0.2 mL 3% sucrose solution each day, which contained 10 mg/kg/BW/d rosiglitazone |
| SC | 6 | 20 weeks | High-fat feed | Administering intragastrically with 0.2 mL 3% sucrose solution each day, which contained 3 mg/kg/BW/d simvastatin |
| 8630 | 6 | 20 weeks | High-fat feed | Administering intragastrically with 0.2 mL 3% sucrose solution each day, which contained $1.0 \times 10^9$ CFU/mL CCFM8630 |
| 8631 | 6 | 20 weeks | High-fat feed | Administering intragastrically with 0.2 mL 3% sucrose solution each day, which contained $1.0 \times 10^9$ CFU/mL CCFM8631 |
| 8630 + 8631 | 6 | 20 weeks | High-fat feed | Administering intragastrically with 0.2 mL 3% sucrose solution each day, which contained $1.0 \times 10^9$ CFU/mL CCFM8630 + CCFM8631 |
| 8630 + 8631 + 1044 + 711 | 6 | 20 weeks | High-fat feed | Administering intragastrically with 0.2 mL 3% sucrose solution each day, which contained $1.0 \times 10^9$ CFU/mL CCFM8630 + CCFM8631 + CCFM1044 + CCFM711 |

At the end of the experiment in 20th week, the mice were fasted, but available to water for 12 h, and anesthetized with ketamine (100 mg/kg bw) by intraperitoneal injection. Blood was collected from the eyeballs, and the mice were sacrificed by dislocation. The blood was centrifuged under conditions of 4° C., 3000 g for 10 min. The supernatant, i.e., the serum, was collected carefully with a small-scale pipette, and froze and stored at −80° C. A fully automatic biochemical analyser was used to measure the serum LDL-C, TC, ALT, AST and ALP contents. The liver was rinsed with normal saline, and a part of liver was used to prepare a 10% liver homogenate, which was froze and stored at −80° C. The liver TG level was measured according to the specifications of Nanjing Jiancheng kit.

The experimental results were shown in FIG. 1. Compared with NC group, serum LDL-C content in mice having metabolic syndrome in the HF group increased significantly (P<0.0001). In the intervention groups, compared with the HF group, the LDL-C contents of the RH, SC, 8630, 8631, 8630+8631 and 8630+8631+1044+711 (the ratio of viable count was 1:1:1:1) groups respectively decreased in an extent of 0.328 mmol/L, 0.28 mmol/L, 0.224 mmol/L, 0.184 mmol/L, 0.256 mmol/L and 0.324 mmol/L. The LDL-C level of 8630+8631+1044+711 group (the ratio of viable count was 1:1:1:1) was lower than that in the SC group and other probiotic intervention group. Compared with the 8630 group, 8631 group and 8630+8631 group, the extent of decrease respectively increased by 44.64%, 76.09% and 26.56%, indicating that the CCFM8630+CCFM8631+ CCFM1044+CCFM711 had a better effect on decreasing serum LDL-C content of mice having metabolic syndrome.

In view of this, combination of the four probiotics CCFM8630, CCFM8631, CCFM1044 and CCFM711 shows a significant synergistic effect on decreasing the increase of serum LDL-C of mice having high-fat diet-induced metabolic syndrome.

Example 4

Figure 2:
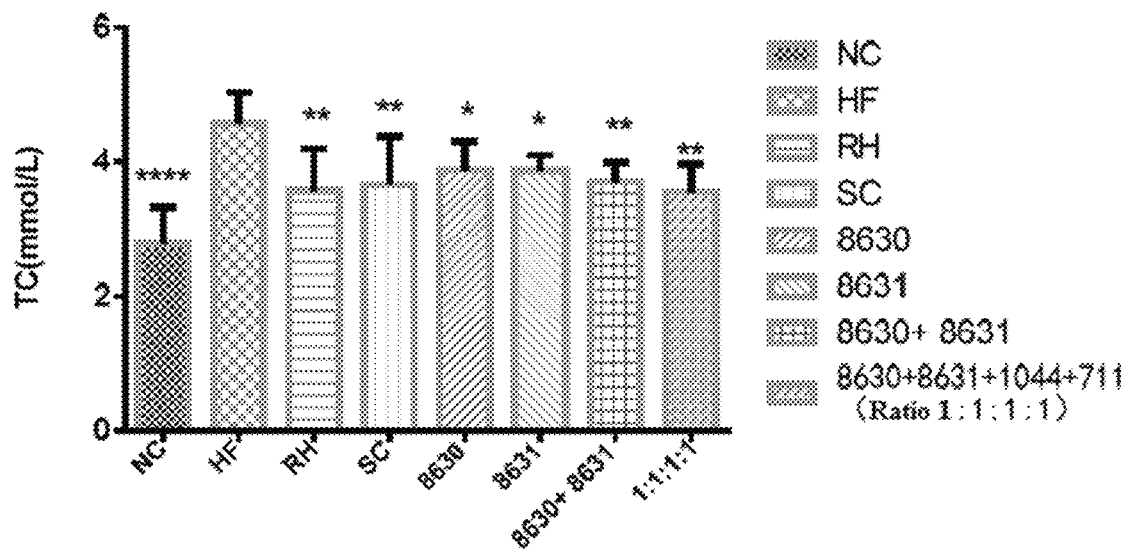
FIG. 2 is a graph showing the effects of different probiotic compounding intervention groups in Example 4 of the present disclosure on alleviating serum TC content increasing in mice having high-fat diet induced metabolic syndrome.

Influence of Composite Probiotics on Serum TC of Mouse Having High-Fat Diet-Induced Metabolic Syndrome C57BL/6J mice were grouped, modeled and treated in the same manner as those in Example 3. The experimental results were shown in FIG. 2.

Compared with the NC group, TC in mice of HF group increased significantly (P<0.0001). In the intervention groups, compared with the HF group, the TC contents of the RH, SC, 8630, 8631, 8630+8631 and 8630+8631+1044+711 (the ratio of viable count was 1:1:1:1) groups all significantly decreased, in an extent of respectively 0.996 mmol/L, 0.912 mmol/L, 0.696 mmol/L, 0.706 mmol/L, 0.872 mmol/L and 1.016 mmol/L. The TC content of the 8630+8631+1044+711 group (the ratio of viable count was 1:1:1:1) was lower than that in the drug group and other probiotic intervention group. Compared with the 8630 group, 8631 group and 8630+8631 group, the extent of decrease respectively increased by 45.98%, 67.66% and 16.51%, indicating that the CCFM8630+CCFM8631+CCFM1044+CCFM711 had a better effect on decreasing serum TC content of mice having metabolic syndrome.

In view of this, combination of the four probiotics CCFM8630, CCFM8631, CCFM1044 and CCFM711 shows a significant synergistic effect on decreasing the increase of serum TC of mice having high-fat diet-induced metabolic syndrome.

Example 5

Figure 3:
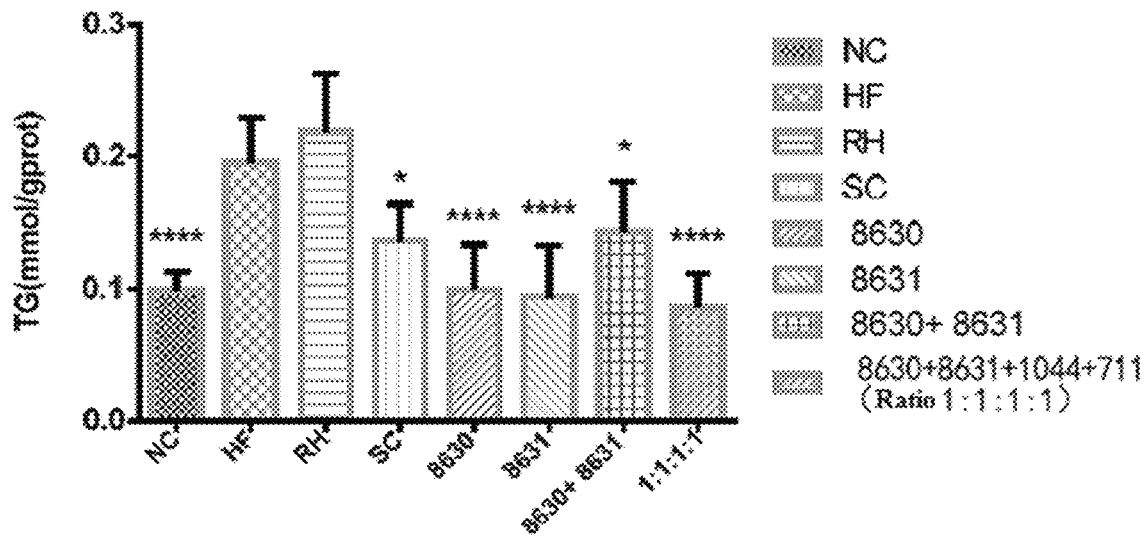
FIG. 3 is a graph showing the effects of different probiotic compounding intervention groups in Example 5 of the present disclosure on alleviating liver TG content increasing in mice having high-fat diet induced metabolic syndrome.

Influence of Composite Probiotics on Liver TG Level of Mouse Having High-Fat Diet-Induced Metabolic Syndrome C57BL/6J mice were grouped, modeled and treated in the same manner as those in Example 3. The experimental results were shown in FIG. 3.

Compared with the NC group, TG in mice of HF group increased significantly ($P<0.0001$). In the intervention groups, compared with the HF group, the TG contents of the SC, 8630, 8631, 8630+8631 and 8630+8631+1044+711 (the ratio of viable count was 1:1:1:1) groups all significantly decreased, in an extent of respectively 0.059 mmol/L, 0.096 mmol/L, 0.1012 mmol/L, 0.052 mmol/L and 0.1092 mmol/L. The TC content of the 8630+8631+1044+711 group (the ratio of viable count was 1:1:1:1) was lower than that in the SC group and other probiotic intervention group. Compared with the 8630 group, 8631 group and 8630+8631 group, the extent of decrease respectively increased by 13.75%, 7.91% and 110%, indicating that the CCFM8630+CCFM8631+CCFM1044+CCFM711 had a better effect on decreasing liver TG content of mice having metabolic syndrome.

In view of this, combination of the four probiotics CCFM8630, CCFM8631, CCFM1044 and CCFM711 shows a significant synergistic effect on decreasing the increase of liver TG level of mice having high-fat diet-induced metabolic syndrome.

Example 6

Figure 4:
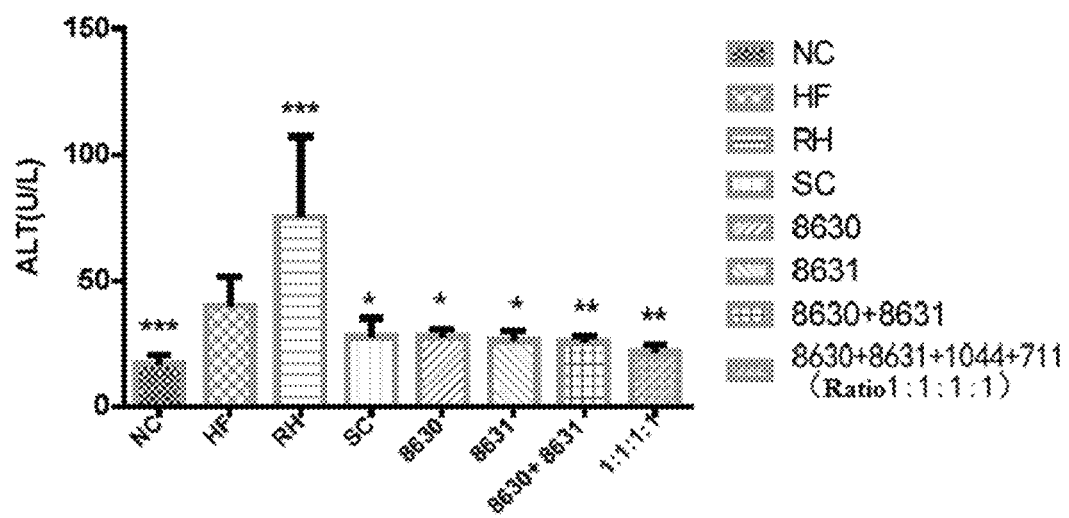
FIG. 4 is a graph showing the effects of different probiotic compounding intervention groups in Example 6 of the present disclosure on alleviating serum ALT level increasing in mice having high-fat diet induced metabolic syndrome.
Figure 5:
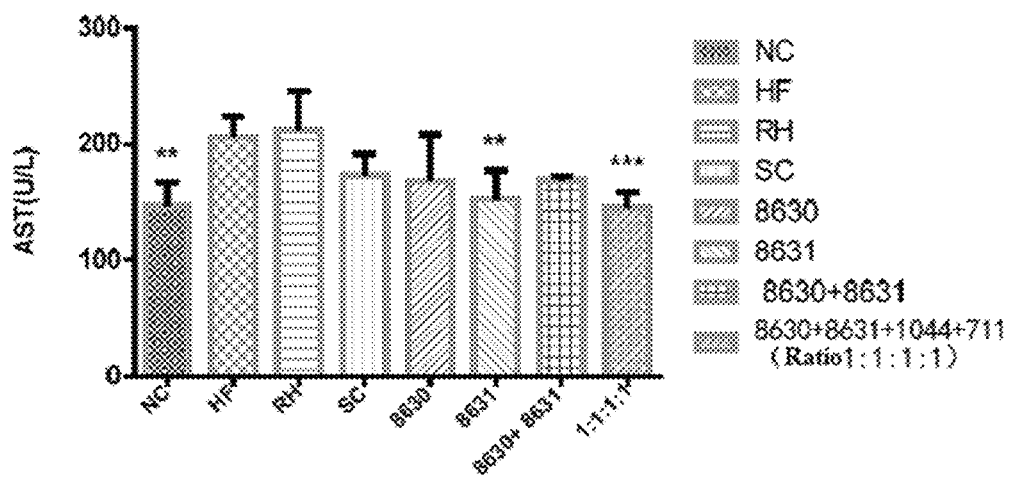
FIG. 5 is a graph showing the effects of different probiotic compounding intervention groups in Example 6 of the present disclosure on alleviating the serum AST level increasing in mice having high-fat diet induced metabolic syndrome.
Figure 6:
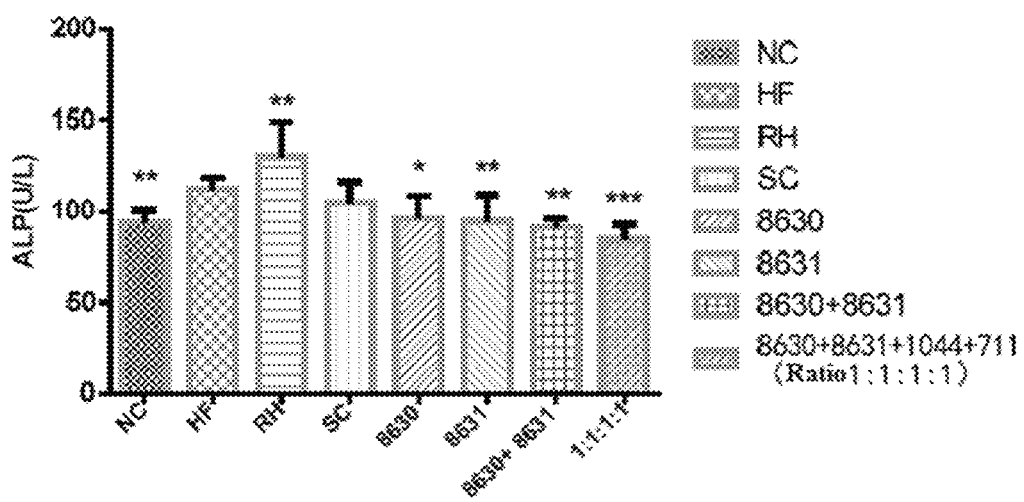
FIG. 6 is a graph showing the effects of different probiotic compounding intervention groups in Example 6 of the present disclosure on alleviating the serum ALP level increasing in mice having high-fat diet induced metabolic syndrome.

Influence of Composite Probiotics on Serum Alanine Aminotransferase (ALT), Aspartate Aminotransferase (AST) and Alkaline Phosphatase (ALP) of Mouse Having High-Fat Diet-Induced Metabolic Syndrome C57BL/6J mice were grouped, modeled and treated in the same manner as those in Example 3. The experimental results were shown in FIGS. 4, 5 and 6.

Compared with the NC group, ALT levels in mice having metabolic syndrome of HF group increased significantly ($P<0.0001$). In the intervention groups, compared with the HF group, the ALT levels of the SC, 8630, 8631, 8630+8631 and 8630+8631+1044+711 (the ratio of viable count was 1:1:1:1) groups all significantly decreased, in an extent of respectively 12.48 U/L, 12.48 U/L, 13.84 U/L, 14.64 U/L and 18.58 U/L. The ALT level of the 8630+8631+1044+711 group (the ratio of viable count was 1:1:1:1) was lower than that in the SC group and other probiotic intervention group. Compared with the 8630 group, 8631 group and 8630+8631 group, the extent of decrease respectively increased by 48.88%, 34.25% and 26.91%, indicating that the CCFM8630+CCFM8631+CCFM1044+CCFM711 had a better effect on decreasing serum ALT levels of mice having metabolic syndrome.

Compared with the NC group, serum AST levels in mice having metabolic syndrome of HF group increased significantly ($P<0.001$). In the intervention groups, compared with the HF group, the AST of both of the 8631 and 8630+8631+1044+711 (the ratio of viable count was 1:1:1:1) groups significantly decreased, in an extent of respectively 53.36 U/L and 60.64 U/L. Compared with the 8631 group, the extent of decrease of the 8630+8631+1044+711 group (the ratio of viable count was 1:1:1:1) increased by 13.64%, indicating that the CCFM8630+CCFM8631+CCFM1044+CCFM711 had a better effect on decreasing serum AST levels of mice having metabolic syndrome.

Compared with the NC group, ALP levels in mice having metabolic syndrome of HF group increased significantly ($P<0.05$). In the intervention groups, compared with the HF group, the ALP levels of the 8630, 8631, 8630+8631 and 8630+8631+1044+711 (the ratio of viable count was 1:1:1:1) groups all significantly decreased, in an extent of respectively 16 U/L, 17.6 U/L, 20.8 U/L and 27.2 U/L. The ALP level of the 8630+8631+1044+711 group (the ratio of viable count was 1:1:1:1) was lower than that in other probiotic intervention group. Compared with the 8630 group, 8631 group and 8630+8631 group, the extent of decrease respectively increased by 70%, 54.55% and 30.77%, indicating that the CCFM8630+CCFM8631+CCFM1044+CCFM711 had a better effect on decreasing serum ALP levels of mice having metabolic syndrome.

In view of this, combination of the four probiotics CCFM8630, CCFM8631, CCFM1044 and CCFM711 shows a significant synergistic effect on decreasing the increase of serum alanine aminotransferase (ALT), aspartate aminotransferase (AST) and alkaline phosphatase (ALP) of mice having high-fat diet-induced metabolic syndrome.

Example 7

Figure 7:
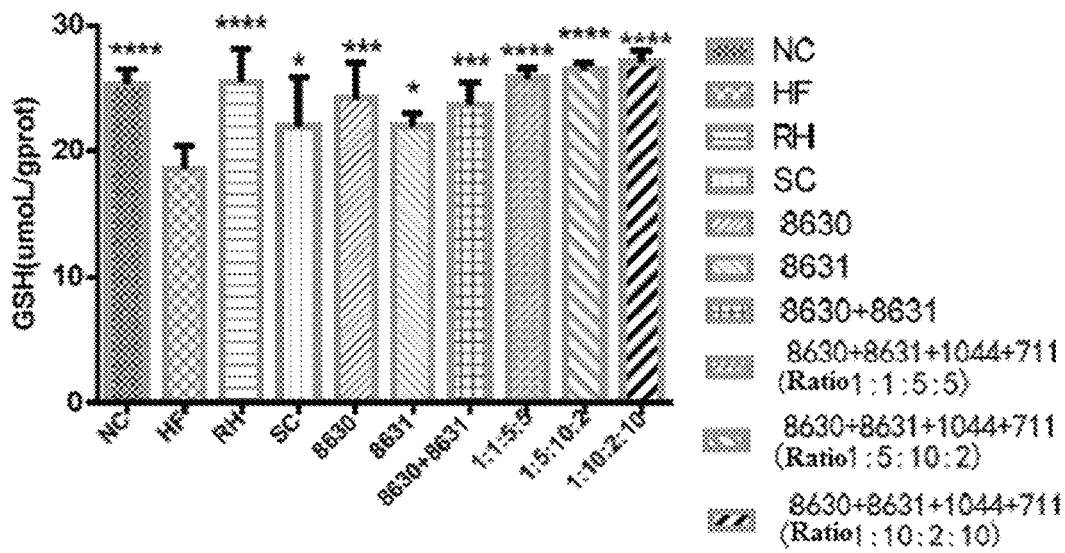
FIG. 7 is a graph showing the effects of different probiotic compounding intervention groups in Example 7 of the present disclosure on alleviating the liver glutathione content decreasing in mice having high-fat diet induced metabolic syndrome.
Figure 8:
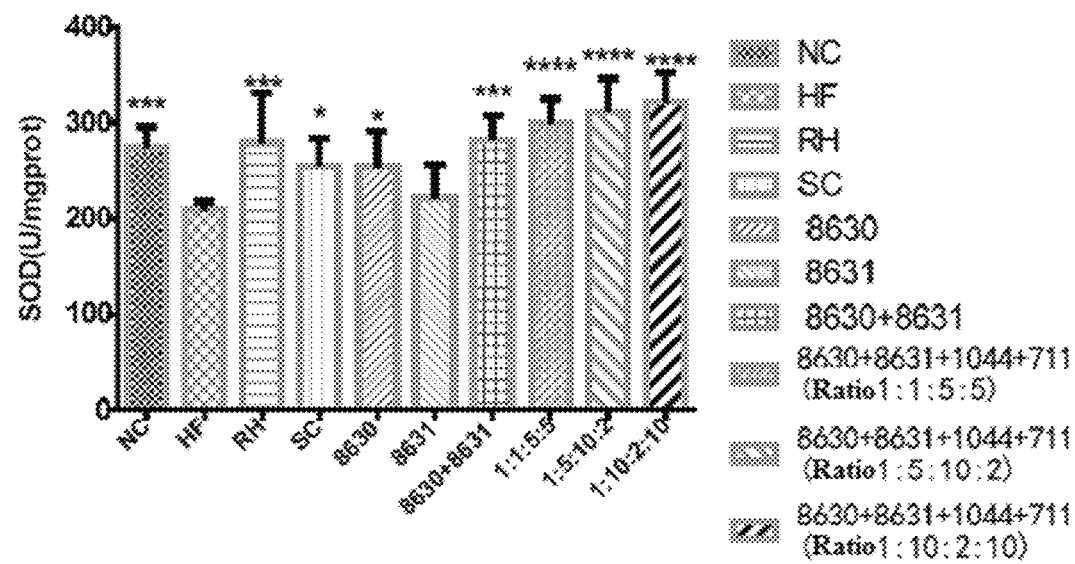
FIG. 8 is a graph showing the effects of different probiotic compounding intervention groups in Example 7 of the present disclosure on alleviating the liver superoxide dismutase content decreasing in mice having high-fat diet induced metabolic syndrome.

Influence of Composite Probiotics on Liver Glutathione (GSH) and Superoxide Dismutase (SOD) of Mouse Having High-Fat Diet-Induced Metabolic Syndrome C57BL/6J mice were modeled in the same manner as that in Example 3. The ratio of viable count of *Bifidobacterium adolescentis* CCFM8630, *Lactobacillus reuteri* CCFM8631, *Lactobacillus rhamnosus* CCFM1044 and *Lactobacillus casei* CCFM711 were changed from 1:1:1:1 to 1:1:5:5, 1:5:10:2 and 1:10:2:10, and the total viable count remained to be $1.0 \times 10^9$ CFU/mL. The glutathione and superoxide dismutase contents in mouse liver were measured according to the specifications of Nanjing Jiancheng glutathione and superoxide dismutase kit. The experimental results were shown in FIGS. 7 and 8.

Compared with the NC group, GSH in mice of the HF group increased significantly ($P<0.001$). In the intervention groups, compared with the HF group, the GSH levels of the SC, 8630, 8631, 8630+8631, 8630+8631+1044+711 (the ratio of viable count was 1:1:5:5), 8630+8631+1044+711 (the ratio of viable count was 1:5:10:2) and 8630+8631+1044+711 (the ratio of viable count was 1:10:2:10) groups significantly increased, in an extent of respectively 6.88 µmoL/g prot, 3.43 µmoL/g prot, 5.63 µmoL/g prot, 3.39 µmoL/g prot, 5.11 µmoL/g prot, 7.18 µmoL/g prot, 7.92 µmoL/g prot and 8.56 µmoL/g prot. The GSH levels of each 8630+8631+1044+711 formulation group were higher than that in the drug groups and other probiotic intervention group. Compared with the 8630 group, 8631 group and 8630+8631 group, the extent of increase of the 8630+8631+1044+711 (the ratio of viable count was 1:1:5:5) group respectively increased by 27.50%, 112.11% and 40.68%. Compared with the 8630 group, 8631 group and 8630+8631 group, the extent of increase of the 8630+8631+1044+711 (the ratio of viable count was 1:5:10:2) group respectively increased by 40.50%, 133.74% and 55.02%. Compared with the 8630 group, 8631 group and 8630+8631 group, the extent of increase of the 8630+8631+1044+711 (the ratio of viable count was 1:10:2:10) group respectively increased by 51.91%, 152.71% and 67.61%, indicating that the CCFM8630+CCFM8631+CCFM1044+CCFM711 had a better effect on increasing liver GSH levels of mice having metabolic syndrome.

Compared with the NC group, the SOD activity in mice of the HF group decreased significantly (P<0.001). In the intervention groups, compared with the HF group, the SOD activity of the SC, 8630, 8631, 8630+8631, 8630+8631+1044+711 (the ratio of viable count was 1:1:5:5), 8630+8631+1044+711 (the ratio of viable count was 1:5:10:2) and 8630+8631+1044+711 (the ratio of viable count was 1:10:2:10) groups all increased, in an extent of respectively 70.07 U/mg prot, 46.11 U/mg prot, 45.29 U/mg prot, 11.96 U/mg prot, 72.99 U/mg prot, 90.78 U/mg prot, 102.12 U/mg prot and 112.06 U/mg prot. The SOD activities of each 8630+8631+1044+711 formulation group were higher than that in the drug groups and other probiotic intervention group. Compared with the 8630 group, 8631 group and 8630+8631 group, the extent of increase of the 8630+8631+1044+711 (the ratio of viable count was 1:1:5:5) group respectively increased by 100.44%, 659.32% and 24.37%. Compared with the 8630 group, 8631 group and 8630+8631 group, the extent of increase of the 8630+8631+1044+711 (the ratio of viable count was 1:5:10:2) group respectively increased by 125.48%, 754.19% and 39.91%. Comparing with the 8630 group, 8631 group and 8630+8631 group, the extent of increase of the 8630+8631+1044+711 (the ratio of viable count was 1:10:2:10) group respectively increased by 147.42%, 837.31% and 53.52%, indicating that the CCFM8630+CCFM8631+CCFM1044+CCFM711 had a better effect on increasing liver SOD activities of mice having metabolic syndrome.

In view of this, combination of the four probiotics CCFM8630, CCFM8631, CCFM1044 and CCFM711 shows a significant synergistic effect on recovering the decrease of liver glutathione (GSH) and superoxide dismutase (SOD) activities of mice having high-fat diet-induced metabolic syndrome.

Example 8

Figure 9:
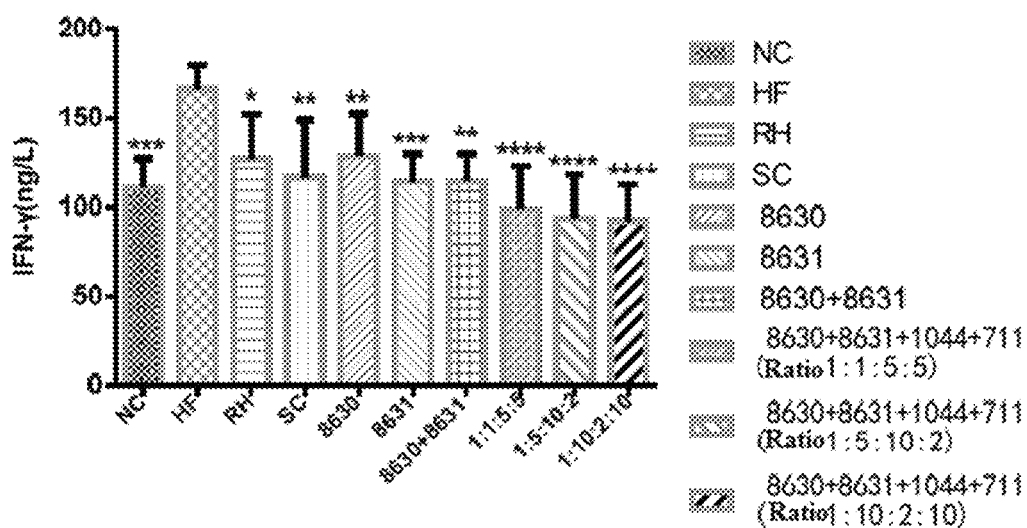
FIG. 9 is a graph showing the effects of different probiotic compounding intervention groups in Example 8 of the present disclosure on alleviating the serum IFN-γ level increasing in mice having high-fat diet induced metabolic syndrome.

Influence of Composite Probiotic on Serum IFN-γ of Mouse Having High-Fat Diet-Induced Metabolic Syndrome C57BL/6J mice were modeled in the same manner as that in Example 3. The ratio of viable count of *Bifidobacterium adolescentis* CCFM8630, *Lactobacillus reuteri* CCFM8631, *Lactobacillus rhamnosus* CCFM1044 and *Lactobacillus casei* CCFM711 were changed from 1:1:1:1 to 1:1:5:5, 1:5:10:2 and 1:10:2:10, and the total viable count remained to be $1.0 \times 10^9$ CFU/mL. The IFN-γ in mice was measured according to the specifications of Nanjing Senbeijia IFN-γ kit. The experimental results were shown in FIG. 9.

Compared with the NC group, the IFN-γ in mice of HF group increased significantly (P<0.001). In the intervention groups, compared with the HF group, the IFN-γ contents of the RH, SC, 8630, 8631, 8630+8631, 8630+8631+1044+711 (the ratio of viable count was 1:1:5:5), 8630+8631+1044+711 (the ratio of viable count was 1:5:10:2) and 8630+8631+1044+711 (the ratio of viable count was 1:10:2:10) groups all significantly decreased, in an extent of respectively 39.06 ng/L, 49.24 ng/L, 37.63 ng/L, 51.91 ng/L, 51.70 ng/L, 67.17 ng/L, 72.41 ng/L and 74.2 ng/L. The IFN-γ contents of each 8630+8631+1044+711 formulation group were lower than that in the drug groups and other probiotic intervention group. Compared with the 8630 group, 8631 group and 8630+8631 group, the extent of decrease of the 8630+8631+1044+711 (the ratio of viable count was 1:1:5:5) group respectively increased by 78.51%, 29.39% and 29.93%. Compared with the 8630 group, 8631 group and 8630+8631 group, the extent of decrease of the 8630+8631+1044+711 (the ratio of viable count was 1:5:10:2) group respectively increased by 92.44%, 39.49% and 40.07%. Compared with the 8630 group, 8631 group and 8630+8631 group, the extent of decrease of the 8630+8631+1044+711 (the ratio of viable count was 1:10:2:10) group respectively increased by 97.19%, 42.93% and 43.52%, indicating that the CCFM8630+CCFM8631+CCFM1044+CCFM711 had a better effect on decreasing serum IFN-γ content of mice having metabolic syndrome.

In view of this, combination of the four probiotics CCFM8630, CCFM8631, CCFM1044 and CCFM711 shows a significant synergistic effect on alleviating the increase of serum IFN-γ of mice having high-fat diet-induced metabolic syndrome.

The invention claimed is:

1. A method for alleviating metabolic syndrome, comprising administering a composite probiotics to a subject in need thereof, wherein the composite probiotics consists of *Bifidobacterium adolescentis* CCFM8630, *Lactobacillus reuteri* CCFM8631, *Lactobacillus rhamnosus* CCFM1044 and *Lactobacillus casei* CCFM711, and wherein in the composite probiotics, a ratio of a viable count of the *Bifidobacterium adolescentis* CCFM8630, the *Lactobacillus reuteri* CCFM8631, the *Lactobacillus rhamnosus* CCFM1044 and the *Lactobacillus casei* CCFM711 is 1:1-10:1-10:1-10.

2. The method according to claim 1, wherein the composite probiotics are in the form of a food or a medicine.

3. The method according to claim 2, wherein the food is a fermented food.

* * * * *